(12) United States Patent
Terrill et al.

(10) Patent No.: US 9,114,328 B2
(45) Date of Patent: Aug. 25, 2015

(54) REACTIVE DISTILLATION OF A CARBOXYLIC ACID AND A GLYCOL

(75) Inventors: Daniel Latham Terrill, Bristol, TN (US); Kelley Margaret Moran, Kingsport, TN (US); Stephen Neal Falling, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 374 days.

(21) Appl. No.: 13/473,126

(22) Filed: May 16, 2012

(65) Prior Publication Data
US 2013/0310598 A1 Nov. 21, 2013

(51) Int. Cl.
| | | |
|---|---|---|
| C07C 69/68 | (2006.01) |
| B01D 3/00 | (2006.01) |
| C07C 29/149 | (2006.01) |
| C07C 67/08 | (2006.01) |
| C07C 51/12 | (2006.01) |
| C07C 67/54 | (2006.01) |
| C07C 51/44 | (2006.01) |

(52) U.S. Cl.
CPC .............. *B01D 3/009* (2013.01); *C07C 29/149* (2013.01); *C07C 51/12* (2013.01); *C07C 51/44* (2013.01); *C07C 67/08* (2013.01); *C07C 67/54* (2013.01)

(58) Field of Classification Search
CPC ....... C07C 67/08; C07C 29/149; B01D 3/009
See application file for complete search history.

(56) References Cited

U.S. PATENT DOCUMENTS

| | | | |
|---|---|---|---|
| 2,152,852 A | 4/1939 | Loder | |
| 2,158,107 A | 5/1939 | Carruthers et al. | |
| 2,211,624 A | 8/1940 | Loder et al. | |
| 2,211,625 A | 8/1940 | Loder | |
| 2,573,701 A | 11/1951 | Filachione et al. | |
| 2,686,797 A | 8/1954 | Bersworth et al. | |
| 3,859,349 A | 1/1975 | Cody | |
| 3,948,977 A | 4/1976 | Suzuki | |
| 4,087,470 A * | 5/1978 | Suzuki ........................ 568/864 |
| 4,502,923 A | 3/1985 | Dyroff et al. | |
| 4,602,102 A | 7/1986 | Yeakey et al. | |
| 4,867,849 A | 9/1989 | Cova et al. | |
| 5,217,582 A | 6/1993 | Heinsohn et al. | |
| 5,900,491 A | 5/1999 | Kurashima et al. | |
| 6,362,265 B1 | 3/2002 | Wo et al. | |
| 6,998,462 B2 | 2/2006 | Duan et al. | |
| 7,005,536 B2 | 2/2006 | Hayashi et al. | |
| 7,122,698 B2 * | 10/2006 | Yoshida et al. ............... 560/179 |
| 7,186,272 B2 | 3/2007 | Heller | |
| 2004/0122240 A1 * | 6/2004 | Yamane et al. ............... 549/274 |
| 2005/0096481 A1 | 5/2005 | Hildebrandt et al. | |
| 2006/0079711 A1 | 4/2006 | Hayashi et al. | |

FOREIGN PATENT DOCUMENTS

| | | |
|---|---|---|
| GB | 1222008 A | 2/1971 |
| JP | 56122321 A | 9/1981 |
| JP | 57118533 A | 7/1982 |
| JP | 2004182645 A | 7/2004 |
| WO | 2009/140850 A1 | 11/2009 |

OTHER PUBLICATIONS

Co-Pending U.S. Appl. No. 13/491,954, filed Jun. 8, 2012, Mesfin Ejerssa Janka.

Gerberich, H. Robert, et al., "Formaldehyde", Kirk-Othmer Encyclopedia of Chemical Technology, vol. 11, 4$^{th}$ Edition, 1994, pp. 929-950.

Seader, J.D., Ph.D, et al., ., "Distillation", Perry's Handbook of Chemical Engineering, Section 13, 7$^{th}$ Ed., McGraw-Hill Book Co. 1999.

Notification of Transmittal of the International Search Report and the Written Opinion of the International Searching Authority, or the Declaration date of mailing Aug. 22, 2013 received in International Application No. PCT/US2013/040268.

Notification of Transmittal of the International Search Report and the Written Opinion of the International Searching Authority, or the Declaration date of mailing Oct. 11, 2013 received in International Application No. PCT/US2013/042348.

* cited by examiner

*Primary Examiner* — Paul A Zucker
(74) *Attorney, Agent, or Firm* — Jennifer R. Knight

(57) ABSTRACT

Disclosed is a process for producing glycolate ester oligomers. The process comprises reacting ethylene glycol and glycolic acid to produce a stream of glycolate ester oligomers and glycolic acid oligomers while simultaneously removing water. The stream of glycolate ester oligomers and glycolic acid oligomers has a low concentration of water and glycolic acid-ends, and thus is useful in a subsequent hydrogenation reaction to produce ethylene glycol.

17 Claims, 2 Drawing Sheets

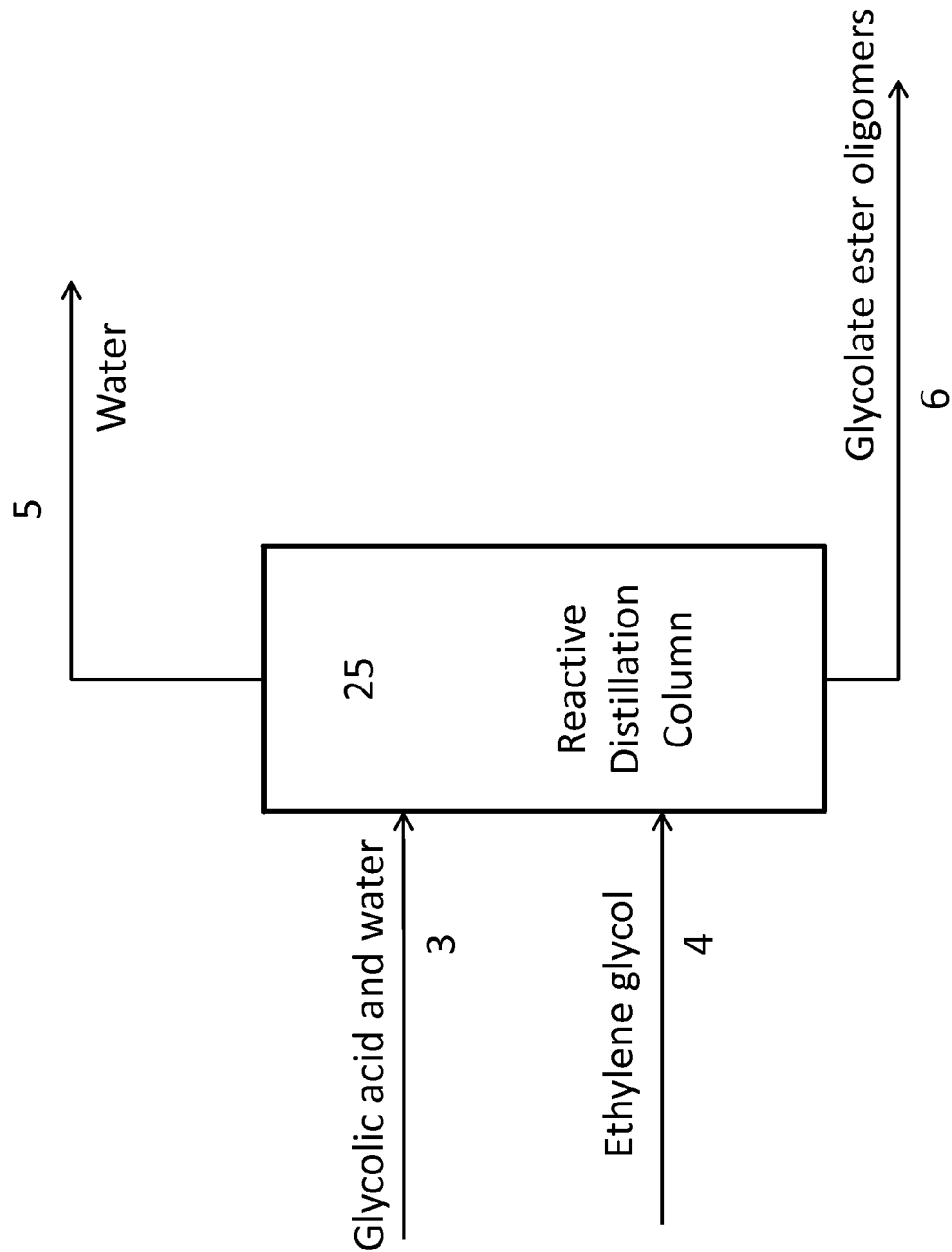
FIGURE 1 - Reactive Distillation Column Schematic

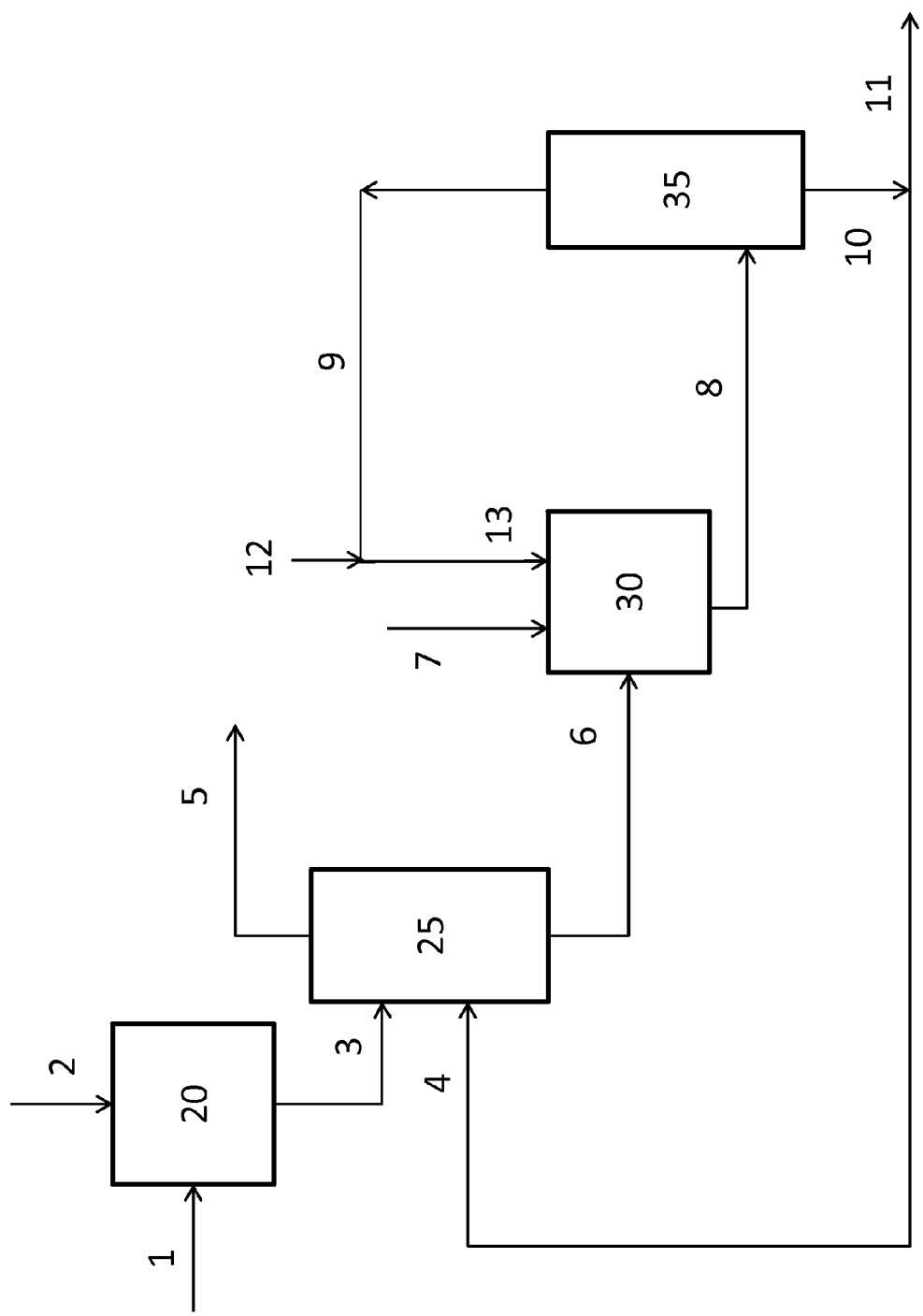
FIGURE 2 - Overall Ethylene Glycol Production Schematic

REACTIVE DISTILLATION OF A CARBOXYLIC ACID AND A GLYCOL

FIELD OF THE INVENTION

This invention pertains to the esterification of aqueous glycolic acid. More particularly, this invention pertains to the reactive distillation of ethylene glycol and glycolic acid wherein water is removed as the distillate product and glycolate esters are removed as the bottoms product. When utilized within a process for making ethylene glycol from glycolic acid, part of the ethylene glycol product can be recycled as the ethylene glycol feed to the reactive distillation column.

BACKGROUND OF THE INVENTION

Glycolic acid (also known as 2-hydroxyacetic acid or α-hydroxyacetic acid) can be used to make ethylene glycol. Glycolic acid can be produced by the reaction of aqueous formaldehyde and carbon monoxide in the presence of an acid catalyst. This reaction is often referred to as the "hydrocarboxylation" or "carbonylation" of formaldehyde. The formaldehyde reactant is generally prepared by well-known methods as an aqueous mixture that contains 35 to 70 weight percent formaldehyde. Typically the glycolic acid is first esterified with an alcohol, diol, or other polyol to produce glycolate ester oligomers which are then hydrogenated to produce ethylene glycol. The esterification step leads to faster reaction rates and better selectivity to ethylene glycol at milder operating conditions of temperature and pressure than applying hydrogenation of glycolic acid directly.

Esterifying glycolic acid and ethylene glycol produces a mixture of glycolate ester oligomers and glycolic acid oligomers. One of the products of these many reactions is water. The presence of water is undesirable for at least two reasons. The esterification reactions are equilibrium limited, so the removal of water favors the formation of glycolate ester oligomers. Secondly, water serves as a deactivator to the hydrogenation reaction catalyst in the process for making ethylene glycol. The hydrogenation catalyst deactivation not only is affected by water in the feed, but also water produced in the hydrogenation reactor. Each mole of glycolic acid and glycolic acid oligomers (i.e., each mole of acid-ends) in the feed produces one mole of water upon hydrogenation. There is a need in the industry to esterify glycolic acid such that the product stream has a limited amount of total moles of water plus acid-ends. There is also a need to produce glycolate ester oligomers for hydrogenation in a manner that is more economical in the overall process for producing ethylene glycol from glycolic acid.

SUMMARY OF THE INVENTION

We have discovered that the equilibrium limited esterification of glycolic acid can be enhanced by reacting a hydroxyl compound such as ethylene glycol and glycolic acid while simultaneously removing water from the reaction. Thus one embodiment of our invention is a process for producing glycolate ester oligomers comprising the steps of (a) feeding ethylene glycol, glycolic acid, and water to a reaction zone; (b) reacting the ethylene glycol and the glycolic acid to produce glycolate ester oligomers and glycolic acid oligomers; (c) removing an overhead stream comprising water from the reaction zone; and (d) removing an effluent comprising the glycolate ester oligomers and the glycolic acid oligomers from the reaction zone. The effluent comprises less than 20 mole percent of the total moles of water plus acid-ends.

Another embodiment of the invention is a process for producing glycolate ester oligomers comprising the steps of (a) feeding ethylene glycol, glycolic acid, and water to a distillation column; (b) reacting the ethylene glycol and the glycolic acid to produce glycolate ester oligomers and glycolic acid oligomers; (c) removing a distillate product comprising water from the distillation column; and (d) removing a bottoms product comprising the glycolate ester oligomers and the glycolic acid oligomers from the distillation column. The bottoms product comprises less than 20 mole percent of the total moles of water plus acid-ends.

Another embodiment of the invention is a process for the production of ethylene glycol comprising the steps of (a) preparing an acid stream comprising glycolic acid by contacting formaldehyde with carbon monoxide and water; (b) feeding the acid stream and a first ethylene glycol stream to a distillation column to produce a distillate product comprising water and a bottoms product comprising glycolate ester oligomers and glycolic acid oligomers; (c) feeding the bottoms product and hydrogen to a hydrogenation reactor to produce a second ethylene glycol stream; (d) separating the second ethylene glycol stream into the first ethylene glycol stream and a product stream; and (e) recycling at least a portion of the first ethylene glycol stream to the distillation column in step (b).

DESCRIPTION OF THE DRAWINGS

FIG. 1 is a schematic of an embodiment of the present invention using a reactive distillation column.

FIG. 2 is a schematic of an embodiment of the present invention including the hydrocarboxylation of formaldehyde, esterification of glycolic acid with ethylene glycol in a reactive distillation column, hydrogenation of glycolate ester oligomers, and recycle of a portion of the ethylene glycol to the esterification step.

DETAILED DESCRIPTION

The present invention provides a process for producing glycolate ester oligomers comprising the steps of (a) feeding ethylene glycol, glycolic acid, and water to a reaction zone; (b) reacting the ethylene glycol and the glycolic acid to produce glycolate ester oligomers and glycolic acid oligomers; (c) removing an overhead stream comprising water from the reaction zone; and (d) removing an effluent comprising the glycolate ester oligomers and the glycolic acid oligomers from the reaction zone. The effluent comprises less than 20 mole percent of the total moles of water plus acid-ends.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "glycolic acid", as used herein, refers to the chemical compound, glycolic acid, also known as 2-hydroxyacetic acid. The term "glycolic acid oligomers", as used herein, refers to the reaction products of glycolic acid with itself, particularly the linear or cyclic esters formed by a reaction between the carboxyl group of one molecule and the alcohol group of another molecule. The "glycolic acid oligomers" include, but are not limited to, (2-hydroxyacetoxy) acetic acid (G2), 2-(2'-hydroxyacetoxy)acetoxyacetic acid (G3), and 2-(2'-(2"-hydroxyacetoxy)acetoxy)acetoxyacetic acid (G4). Typically, glycolic acid oligomers with two to four glycolic acid repeats will be present with glycolic acid at temperatures used for the "reactions of ethylene glycol and glycolic acid". The terms "reactions of ethylene glycol and glycolic acid", and "reacting ethylene glycol and glycolic acid", as used herein, refer to the many reactions that occur when ethylene glycol and glycolic acid are present at typical reaction conditions. The reactions include reactions between ethylene glycol and glycolic acid and glycolic acid with itself. Additionally the reactions include reactions between ethylene glycol, glycolic acid, and glycolic acid oligomers or other reaction products such as 2-hydroxyethyl 2-hydroxyacetate. The term "glycolate ester oligomers", as used herein, refers to the many reaction products of glycolate esters formed by "reacting ethylene glycol and glycolic acid". Examples include, but are not limited to 2-hydroxyethyl 2-hydroxyacetate, 1,2-ethanediyl bis(2-hydroxyacetate), 2'-[2"-(2'''-hydroxyacetoxy)acetoxy]ethyl 2-hydroxyacetate, 2'-(2"-[2'''-(2''''-hydroxyacetoxy)acetoxy]acetoxy)ethyl 2-hydroxyacetate, 2''-hydroxyethyl (2'-hydroxyacetoxy)acetate, 2'''-hydroxyethyl (2'-(2"-hydroxyacetoxy)acetoxy)acetate, 2''''-hydroxyethyl (2'-(2"-(2'''-hydroxyacetoxy)acetoxy)acetoxy)acetate, 2'-[2"-(2'''-hydroxyacetoxy)ethoxy] ethyl 2-hydroxyacetate, and 2'-(2"-hydroxyethoxy)ethyl 2-hydroxyacetate.

The term "mole percent of the total moles of water plus acid-ends" refers to the sum of the moles of water, the moles of glycolic acid, and moles of glycolic acid oligomers divided by the sum of the moles of water, the moles of ethylene glycol moiety, and the moles of glycolic acid moiety. The term "ethylene glycol moiety," as used herein, refers to the O—CH2—CH2—O segment of a molecule. For example, the moles of ethylene glycol moiety in 1,2-ethanediyl bis(2-hydroxyacetate) is one, and the moles of ethylene glycol moiety in 2'-[2"-(2'''-hydroxyacetoxy)ethoxy]ethyl 2-hydroxyacetate is two. The term "glycolic acid moiety," as used herein, refers to the O—CH2—CO2 segment of a molecule. For example, the moles of glycolic acid moiety in 2-hydroxyethyl 2-hydroxyacetate is one, the moles of glycolic acid moiety in 1,2-ethanediyl bis(2-hydroxyacetate) is two, and the moles of glycolic acid moiety in 2'-[2"-(2'''-hydroxyacetoxy)acetoxy] ethyl 2-hydroxyacetate is three.

The term "reaction zone", as used herein, refers to part of the process wherein the "reacting ethylene glycol and glycolic acid" and removing of water simultaneously occur. The term "overhead stream", as used herein, refers to the stream that has been vaporized for removal of water from the reaction zone. The overhead stream may leave the reaction zone as a vapor or may first be condensed to form a liquid. The term "effluent", as used herein, refers to the liquid stream exiting the reaction zone comprising the "glycolate ester oligomers" and "glycolic acid oligomers". The term "distillation column", as used herein, refers to a multi-stage fractionation unit operation wherein the "reactions of ethylene glycol and glycolic acid" and the separation of water occur across the multi-stage unit. The term "distillate product", as used herein, refers to the stream leaving the top of the "distillation column" (often after having been liquefied in a condenser). The term "bottoms product", as used herein, refers to the stream leaving the bottom or base of the "distillation column". The "base temperature" as used herein, refers to the temperature as measured at or near the bottom of a "distillation column", for example, at the base of the column, or of the "bottoms product" as it leaves the "distillation column". The "column pressure", as used herein, refers to the pressure as measured at or near the top of a "distillation column", for example, at the condenser or at the vacuum pump. The term "stages", as used herein, refers to a vapor-liquid contacting device where bubbles of vapor are distributed into a holding volume of boiling liquid. Liquid and vapor flow in counter-current directions. The term "feeding configuration", as used herein, refers to the relative location of the one or more steams feeding the "distillation column". A "lower stage" of the "distillation column" is closer to the bottom and a "higher stage" is closer to the top. For example, if ethylene glycol is fed at a "lower stage" than glycolic acid, then the glycolic acid feed is between the distillate product and the ethylene glycol feed. Conversely if ethylene glycol is fed at "higher stage" than glycolic acid, then the glycolic acid feed is between the ethylene glycol feed and the "bottoms product".

The term "molar ratio", as used herein, refers to the moles of one component divided by the moles of another component. For example, if the molar ratio of glycolic acid to ethylene glycol is 2:1, then for every mole of ethylene glycol, there are two moles of glycolic acid. Note that the water in any aqueous glycolic acid feed is not considered in the molar ratio of glycolic acid to ethylene glycol.

The aqueous glycolic acid mixture may be prepared by any means known to persons skilled in the art such as, for example, by simply dissolving glycolic acid in water or by fermentation methods. Our invention is illustrated, however, with particular reference to esterifying aqueous glycolic acid mixtures prepared by contacting aqueous solutions of formaldehyde with carbon monoxide in the presence of an acid catalyst under elevated pressures and temperatures. These reactions are referred to herein as the "hydrocarboxylation" of formaldehyde and are exemplified in U.S. Pat. Nos. 2,152, 852; 2,153,064; 2,211,624; 2,211,625; and 3,948,977; and United Kingdom Patent No. 1,499,245.

The hydrocarboxylation process can be carried out by feeding carbon monoxide to a reaction mixture comprising aqueous formaldehyde in the presence of an acid catalyst. The carbon monoxide typically is supplied to the reaction mixture in sufficient excess to insure an adequate supply thereof for absorption by the formaldehyde and to retard side reactions such as, for example, the decomposition of the formaldehyde to carbon monoxide and hydrogen or other products. The amount of carbon monoxide useful for the carbonylation reaction ranges from a molar ratio of 0.1:1 to 1,000:1 of carbon monoxide to formaldehyde or formaldehyde equivalents with a more preferred range being from 0.5:1 to 100:1 and a most preferred range from 1.0:1 to 20:1.

The composition of the carbon monoxide stream required for hydrocarboxylation may comprise carbon monoxide, hydrogen, and carbon dioxide. For example, the carbon monoxide may be supplied in substantially pure form or as a mixture with other gases such as, for example, hydrogen, carbon dioxide, methane, nitrogen, noble gases (e.g., helium and argon), and the like. For example, the carbon monoxide need not be of high purity and may contain from 1% by volume to 99% by volume carbon monoxide. The remainder of the gas mixture may include such gases as, for example, nitrogen, hydrogen, water, noble gases, and paraffinic hydrocarbons having from one to four carbon atoms. In order to reduce compression costs, it is desirable for the carbon monoxide stream to comprise at least 95 mole % carbon monoxide, more preferably at least 99 mole %.

The carbon monoxide may be obtained from typical sources that are well known in the art. For example, the carbon monoxide may be provided by any of a number of methods known in the art including steam or carbon dioxide reforming of carbonaceous materials such as natural gas or petroleum derivatives; partial oxidation or gasification of carbonaceous materials, such as petroleum residuum, bituminous, sub bituminous, and anthracitic coals and cokes; lignite; oil shale; oil sands; peat; biomass; petroleum refining residues of cokes; and the like. For example, the carbon monoxide may be provided to the reaction mixture as a component of synthesis gas or "syngas", comprising carbon dioxide, carbon monoxide, and hydrogen.

The aqueous formaldehyde used in the hydrocarboxylation reaction typically comprises 35 to 85 weight percent formaldehyde. Other examples of formaldehyde levels in the aqueous formaldehyde feed are 40 to 70 weight percent and 40 to 60 weight percent. These ranges are typical concentrations that can be achieved with conventional formaldehyde processes without further distillation. Conventional formaldehyde processes are described in "Formaldehyde", Kirk-Othmer Encyclopedia, Vol. 11, 4th Edition, 1994. For example, commercially available formaldehyde typically contains approximately 55 weight percent formaldehyde in water. Other forms of formaldehyde may be present in the aqueous formaldehyde feedstock including trioxane or paraformaldehyde and linear polymers of formaldehyde, i.e., poly(oxymethylene) glycols and derivatives thereof, formed from the polymerization or oligomerization of formaldehyde in water or other solvents. The term "formaldehyde", as used herein, is intended to include all the various forms of formaldehyde described above.

The presence of at least one acid catalyst, although not required for the reaction to proceed, greatly increases the rate of the carbonylation reaction and the increase in rate is at the expense of side reactions. The acid catalyst may be of the Lewis or Brønsted types that are well understood by persons skilled in the art. Acidic catalysts that are active in promoting the carbonylation process generally have pKa values in aqueous solution of less than 7. For example, acid catalysts that have a pKa value in aqueous solution of 5 may be used. Further examples of catalysts are those having a range of pKa values in aqueous solution of −10 to 3, and −10 to 1. Representative examples of acid catalysts are sulfonic acids, mineral acids, solid acids, inorganic acid salts, and combinations thereof. Some more specific examples of acid catalysts include, but are not limited to, hydrochloric acid, phosphoric acid, sulfuric acid, sulfonic acids, acid metal sulfates and acid metal phosphates comprising one or more metals from Groups 1 and 2 of the Periodic Table of the Elements, methanesulfonic acid, trifluoromethanesulfonic acid, boron trifluoride, p-toluenesulfonic acid, benzenesulfonic acid, and combinations thereof.

The acid catalyst may be used in amounts ranging from 0.02 to 1.0 mole of acid catalyst per mole of formaldehyde. Another example of acid catalyst levels is 0.02 to 0.15 mole of acid catalyst per mole of formaldehyde. Proportions higher than 1.0 mole of catalyst per mole of formaldehyde, however, may be used in many instances, such as, for example, in processes in which the catalyst also functions as a solvent. Hydrochloric acid and sulfuric acid may be used in this fashion.

The hydrocarboxylation process can be conducted under continuous, semi-continuous, and batch modes of operation and may utilize a variety of reactor types. Examples of suitable reactor types include, but are not limited to, stirred tank, continuous stirred tank, trickle bed, tower, slurry, and tubular reactors. A typical temperature range for the hydrocarboxylation reaction is 110 to 220° C. In another example, the temperature range can be 190 to 210° C. Examples of pressure ranges for the hydrocarboxylation reaction are 35 to 350 bar gauge and 60 to 200 bar gauge.

The hydrocarboxylation reactants and acid catalyst(s) may be introduced separately or in any sequence or combination to the hydrocarboxylation reactor. In addition, one or more reactants may be introduced at different locations in the reactor. For example, in a continuously operated process containing a catalyst bed, the addition of water or formaldehyde may be staged throughout the reactor. In some cases, it may be desirable to recirculate a portion of the reaction media to the reactor to act as a liquid reaction media for the next synthesis. In order to reduce by-product formation, it is desirable to set the residence time in the hydrocarboxylation reaction to give an outlet formaldehyde concentration of 5 weight percent or less. In addition to glycolic acid, the hydrocarboxylation process typically produces glycolic acid oligomers, water, and unreacted formaldehyde.

For the present invention, when the glycolic acid source is from a hydrocarboxylation process, the aqueous glycolic acid mixture exiting the hydrocarboxylation reactor comprises 50 to 95 weight percent glycolic acid, based on the total weight the reaction mixture. Additional examples of the concentration of glycolic acid in the aqueous mixture are 60 to 90 weight percent and 65 to 90 weight percent. For example, in one embodiment, the aqueous glycolic acid mixture comprises 70 to 90 weight percent glycolic acid and is produced by contacting aqueous formaldehyde with carbon monoxide in the presence of an acid catalyst as described hereinabove.

Glycolic acid can be esterified with an aliphatic hydroxyl compound. Non-limiting examples of the aliphatic hydroxyl compound include, but are not limited to, methanol, ethanol, n-propanol, isopropanol, butanol, Isobutanol, ethylene glycol, diethylene glycol, triethylene glycol, propylene glycol, glycerol, or mixtures thereof. For example, methanol, ethylene glycol, or mixtures thereof may be reacted with glycolic acid to produce glycolate ester oligomers and glycolic acid oligomers. In another example ethylene glycol, diethylene glycol, and/or triethylene glycol may be reacted with glycolic acid to produce glycolate ester oligomers and glycolic acid oligomers. In yet another example, ethylene glycol may be reacted with glycolic acid to produce glycolate ester oligomers and glycolic acid oligomers.

The manner in which ethylene glycol, glycolic acid, and water are fed to the reaction zone is not limiting. The reactants may be fed continuously, semi-continuously, or batch-wise. Reactants may be introduced separately or in any sequence or combination to the reaction zone. In addition, one or more reactants may be introduced at different locations in the reaction zone. For example, in a continuously operated process, the addition of glycolic acid or ethylene glycol may be staged throughout the reaction zone. The glycolic acid may be in an aqueous solution for ease of handling.

The process of the present invention may be conducted under continuous, semi-continuous, or batch modes of operation and may utilize a variety of equipment in the reaction zone. The term "continuous", as used herein, refers to a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start up, reactor maintenance, or scheduled shut down periods. The term "batch" process as used herein means a process wherein all the reactants are added to the reaction zone and then processed according to a predetermined course of reaction during which no material is fed into or removed from the reaction zone with the exception of the removal of water. The term "semi-continuous" means a process where some of the reactants are charged at the beginning of the process and the remaining reactants are fed continuously as the reaction progresses. Alternatively, a semi-continuous process may also include a process similar to a batch process in which all the reactants are added at the beginning of the process except that one or more of the products are removed continuously as the reaction progresses.

The reactions of ethylene glycol and glycolic acid encompasses the several reactions including, but not limited to the following reactions of ethylene glycol with glycolic acid, G2, G3, and G4; as well as glycolic acid reacting further with 2-hydroxyethyl 2-hydroxyacetate (HGEgH), 2"-hydroxyethyl (2'-hydroxyacetoxy)acetate (HG2EgH), and 2'"-hydroxyethyl (2'-(2"-hydroxyacetoxy)acetoxy)acetate (HG3EgH). One mole of water is produced by each of these reactions as well as by the reaction of each glycolic acid to produce G2, G3, and G4. One skilled in the art recognizes that these reactions are equilibrium limited. The vapor pressure of water is higher than the vapor pressure of ethylene glycol, glycolic acid, glycolate ester oligomers, and glycolic acid oligomers. Therefore, heat can be added to the reaction zone to vaporize water which can be removed as an overhead stream. As water is removed, more reactions of ethylene glycol and glycolic acid occur and the liquid of the reaction zone becomes more concentrated in glycolate ester oligomers and glycolic acid oligomers. The effluent from the reaction zone is the reaction product stream comprising the glycolate ester oligomers and glycolic acid oligomers.

The overhead stream comprises water. The overhead stream may also comprise small amounts of glycolic acid and ethylene glycol. For example, the overhead stream may comprise a total amount of ethylene glycol and glycolic acid of less than 10 weight percent, less than 5 weight percent, less than 2.5 weight percent, less than 1 weight percent, less than 0.5 weight percent, or less than 0.1 weight percent, on a total overhead stream weight basis.

In the present invention, the reactions of ethylene glycol and glycolic acid can be carried out to remove water from glycolic acid prior to hydrogenation. The effluent from the reaction zone may contain unremoved water, unreacted ethylene glycol, unreacted glycolic acid, and glycolic acid oligomers in addition to the desired glycolate ester oligomers. Since each mole of glycolic acid as well as each mole of glycolic acid oligomer will produce a mole of water in a downstream hydrogenation reaction, esterification process conditions including but not limited to such things as the molar feed ratio of glycolic acid to ethylene glycol, temperature, and pressure can be optimized to produce an effluent wherein the mole percent of the total moles of water plus acid-ends is less than 20 mole percent, less than 18 mole percent, less than 16 mole percent, less than 14 mole percent, or less than 12 mole percent. In another example, the effluent comprises glycolate ester oligomers and glycolic acid oligomers wherein the mole percent of the total moles of water plus acid-ends is from 5 to 20 mole percent, 5 to 18 mole percent, 5 to 15 mole percent, 5 to 12 mole percent, 7 to 20 mole percent, 7 to 18 mole percent, 7 to 15 mole percent, 9 to 20 mole percent, 9 to 18 mole percent, 9 to 15 mole percent, or 9 to 12 mole percent.

The molar ratio of glycolic acid to ethylene glycol in the feed to the reaction zone affects the economics and operability of the overall process for making ethylene glycol from glycolic acid. On the one hand, if the ratio is too high, there will not be enough ethylene glycol present to remove sufficient water while maintaining soluble, flowable glycolate ester oligomers as the bottoms product. If the ratio is too low, unnecessary expense is encountered by having a recycle ethylene glycol stream that is larger than required. In one aspect of the invention the molar ratio of glycolic acid to ethylene glycol fed to the reaction zone in step (a) is from 0.1:1 to 10:1, 0.1:1 to 5:1, 0.1:1 to 2:1, 0.5:1 to 10:1, 0.5:1 to 5:1, 0.5:1 to 2:1; 1:1 to 10:1, 1:1 to 5:1, or 1:1 to 2:1.

Step (a) may further comprise feeding at least one of the group consisting of methanol, diethylene glycol, and triethylene glycol. In another example, step (a) may further comprise feeding at least one of the group consisting of diethylene glycol and triethylene glycol.

Ethylene glycol and glycolic acid may react to form glycolate ester oligomers in the absence of any additional catalyst. One skilled in the art recognizes that glycolic acid itself can serve as an acid catalyst for the reactions. Alternatively, an esterification catalyst can be used with the present invention. The catalyst may be heterogeneous or homogeneous. Examples of esterification catalysts include, but are not limited to, Brønsted acids such as hydrochloric acid, sulfuric acid, phosphoric acid, methanesulfonic acid, paratoluenesulfonic acid, etc. Lewis acids such as borontrifluoride etherate, aluminum trichloride, zinc oxide, zinc chloride, dibutyltin oxide, tin tetrachloride. Heterogeneous acids such as Nafion-H (DuPont, USA), Amberlyst 15 (Dow, USA), zeolites, Montmorillonite, and niobium oxide. If a catalyst is present it may comprise from 50 ppm to 50 weight percent, 100 ppm to 10 weight percent, 1000 ppm to 5 weight percent, or 0.1 to 1 weight percent of the total weight of the reaction zone contents.

The equipment used in the reaction zone is not particularly limited. Any equipment that has sufficient hold up to allow the esterification reaction to proceed, allow a vapor phase to be produced, and allow for separation of the vapor phase from the liquid phase is suitable. One skilled in the art will recognize that the vapor phase, in this case mostly water, may be condensed before leaving the reaction zone. The reaction zone may comprise at least one piece of equipment selected from the group consisting of an evaporator, a thin-film evaporator, a wiped-film evaporator, a flash vessel, a rectifying column, a stripping column, and a distillation column. In another example, the reaction zone comprises a distillation column.

In an aspect of our invention, the esterification of glycolic acid and simultaneous water removal take place in a distillation column. Therefore, a second embodiment of our invention is a process for producing glycolate ester oligomers comprising the steps of (a) feeding ethylene glycol, glycolic acid, and water to a distillation column; (b) reacting the ethylene glycol and the glycolic acid to produce glycolate ester oligomers and glycolic acid oligomers; (c) removing a distillate product comprising water from the distillation column; and (d) removing a bottoms product comprising the glycolate ester oligomers and the glycolic acid oligomers from the distillation column. The bottoms product comprises less than 20 mole percent of the total moles of water plus acid-ends.

The distillation column can be operated continuously, semi-continuously, or batch wise as these terms are defined above. The manner in which ethylene glycol, glycolic acid, and water are fed to the distillation column is not particularly limited. In one example, the reactants may be combined into a single feed stream and fed anywhere in the distillation column. In another example, ethylene glycol may be fed in a different stream to the distillation column than glycolic acid and water. The ethylene glycol may be fed on a lower stage, on a higher stage, or on the same stage of the distillation column as the glycolic acid and water. The distillation column comprises a reboiler, a condenser, and at least one stage. The type of reboiler and condenser is not limited and many types are known to those skilled in the art. The number of stages for the distillation column is not particularly limited as long as a distillate with little ethylene glycol and glycolic acid and a bottoms product with low water plus acid-ends is produced. In another example, ethylene glycol is fed to the reboiler and glycolic acid and water are fed on a stage. Examples of the number of stages are 2 to 30 stages, 2 to 15 stages, or 2 to 10 stages.

The reaction of ethylene glycol and glycolic acid encompasses the several reactions including, but not limited to the following reactions of ethylene glycol with glycolic acid, G2, G3, and G4; as well as glycolic acid reacting further with 2-hydroxyethyl 2-hydroxyacetate (HGEgH), 2"-hydroxyethyl (2'-hydroxyacetoxy)acetate (HG2EgH), and 2'''-hydroxyethyl (2'-(2"-hydroxyacetoxy)acetoxy)acetate (HG3EgH). One mole of water is produced with each of these reactions as well as for the reaction of each glycolic acid to produce G2, G3, and G4. One skilled in the art recognizes that these reactions are equilibrium limited. The vapor pressure of water is higher than the vapor pressure of ethylene glycol, glycolic acid, glycolate ester oligomers, and glycolic acid oligomers. Therefore, the distillation column can be run with heat added to the reboiler, a vapor stream flowing up the column, a liquid stream flowing down the column, and vapor exiting the column. The vapor may be condensed with part of the condensate exiting as the distillate product and part of the condensate refluxing to the distillation column. As water is removed, the reactions of ethylene glycol and glycolic acid take place and the liquid phase becomes more concentrated in glycolate ester oligomers and glycolic acid oligomers as it gets closer to the bottom of the distillation column. The bottoms product from the distillation column comprises the glycolate ester oligomers and glycolic acid oligomers. The bottoms product also comprises unreacted glycolic acid, unreacted ethylene glycol, as well as water fed to and/or produced in the distillation column.

Step (a) may further comprise feeding at least one of the group consisting of methanol, diethylene glycol, and triethylene glycol. In another example, step (a) may further comprise feeding at least one of the group consisting of diethylene glycol and triethylene glycol.

The distillate product comprises water. The distillate product may also comprise small amounts of glycolic acid and ethylene glycol. For example, the distillate product may comprise a total amount of ethylene glycol and glycolic acid of less than 10 weight percent, less than 5 weight percent, less than 2.5 weight percent, less than 1 weight percent, less than 0.5 weight percent, or less than 0.1 weight percent, on a total distillate product weight basis.

In the present invention, the esterification of glycolic acid can be carried out to remove water from the glycolic acid prior to hydrogenation. The bottoms product from the distillation column may contain unremoved water, unreacted ethylene glycol, unreacted glycolic acid, and glycolic acid oligomers in addition to the desired glycolate ester oligomers. Since each glycolic acid or glycolic acid oligomer may produce a mole of water in a downstream hydrogenation reaction, the total moles of water plus acid-ends (glycolic acid and glycolic acid oligomers) in the bottoms product should be held within a desired range. The distillation column conditions including but not limited to such things as the molar feed ratio of glycolic acid to ethylene glycol, bottoms temperature, column pressure, number of stages, and the like can be optimized to produce a bottoms product wherein the mole percent of the total moles of water plus acid-ends is less than 20 mole percent, less than 18 mole percent, less than 16 mole percent, less than 14 mole percent, or less than 12 mole percent. In another example, the bottoms product comprises glycolate ester oligomers and glycolic acid oligomers wherein the mole percent of the total moles of water plus acid-ends is from 5 to 20 mole percent, 5 to 18 mole percent, 5 to 15 mole percent, 5 to 12 mole percent, 7 to 20 mole percent, 7 to 18 mole percent, 7 to 15 mole percent, 9 to 20 mole percent, 9 to 18 mole percent, 9 to 15 mole percent, or 9 to 12 mole percent.

In one aspect of the invention the molar ratio of the glycolic acid to ethylene glycol fed to the distillation column in step (a) is from 0.1:1 to 10:1, 0.1:1 to 5:1, 0.1:1 to 2:1, 0.5:1 to 10:1, 0.5:1 to 5:1, 0.5:1 to 2:1; 1:1 to 10:1, 1:1 to 5:1, or 1:1 to 2:1.

Ethylene glycol and glycolic acid may react to form glycolate ester oligomers in the absence of any additional catalyst. One skilled in the art recognizes that glycolic acid itself can serve as an acid catalyst for the reactions. Alternatively, an esterification catalyst can be used with the present invention. The catalyst may be heterogeneous or homogeneous. Examples of esterification catalysts include, but are not limited to, Brønsted acids such as hydrochloric acid, sulfuric acid, phosphoric acid, methanesulfonic acid, paratoluenesulfonic acid, etc. Lewis acids such as borontrifluoride etherate, aluminum trichloride, zinc oxide, zinc chloride, dibutyltin oxide, tin tetrachloride. Heterogeneous acids such as Nafion-H (DuPont, USA), Amberlyst 15 (Dow, USA), zeolites, Montmorillonite, and niobium oxide. If a catalyst is present it may comprise from 50 ppm to 50 weight percent, 100 ppm to 10 weight percent, 1000 ppm to 5 weight percent, or 0.1 to 1 weight percent of the total weight of the distillation column contents.

The distillation column may be operated at a base temperature from 100 to 225° C., 100 to 200° C., 100 to 180° C., 150 to 200° C., 150 to 190° C., 150 to 185° C., 150 to 180° C., 150 to 175° C., 160 to 200° C., 160 to 190° C., 160 to 185° C., 160 to 180° C., 160 to 175° C., 165 to 200° C., 165 to 190° C., 165 to 185° C., or 165 to 180° C. The column pressure may be from 5 to 1000 mmHg, 5 to 800 mmHg, 5 to 500 mmHg, 5 to 300 mmHg, 5 to 200 mmHg, 30 to 1000 mmHg, 30 to 800 mmHg, 30 to 500 mmHg, 30 to 300 mmHg, 30 to 200 mmHg, 50 to 1000 mmHg, 50 to 800 mmHg, 50 to 500 mmHg, 50 to 300 mmHg, or 50 to 200 mmHg.

A third embodiment of the invention is a process for the production of ethylene glycol comprising the steps of (a) preparing an acid stream comprising glycolic acid by contacting formaldehyde with carbon monoxide and water; (b) feeding the acid stream and a first ethylene glycol stream to a distillation column to produce a distillate product comprising water and a bottoms product comprising glycolate ester oligomers and glycolic acid oligomers; (c) feeding the bottoms product and hydrogen to a hydrogenation reactor to produce a second ethylene glycol stream; (d) separating the second ethylene glycol stream into the first ethylene glycol stream and a product stream; and (e) recycling at least a portion of the first ethylene glycol stream to the distillation column in step (b).

The various aspects of feeding ethylene glycol, glycolic acid, and water to the distillation column, composition of the bottoms product, the molar ratio of ethylene glycol to glycolic acid fed to the distillation column, the composition of the distillate product, the aspect of no additional catalyst added, the base temperature, the column pressure, and number of stages of the second embodiment apply to this embodiment as well. In another example, the acid stream may be concentrated in glycolic acid and/or glycolic acid oligomers with the removal of part of the water between steps (a) and (b).

In one example, the bottoms product from the distillation column comprises 5 to 18 mole percent of the total moles of water plus acid-ends, the molar feed ratio of glycolic acid to ethylene glycol is from 0.1:1 to 10:1, the base temperature of the distillation column is from 100° C. to 225° C., and the column pressure is from 5 mmHg to 800 mmHg. In another example, the previous conditions are satisfied, and furthermore, the distillation column comprises from 2 to 30 stages and the first ethylene glycol stream is fed at a lower stage than the acid stream is fed.

The glycolate ester oligomers may be hydrogenated as described below to produce ethylene glycol by contacting the glycolate ester oligomers with hydrogen in the presence of a suitable hydrogenation catalyst. The glycolate ester oligomers may be concentrated or purified by means known to one skilled in the art prior to hydrogenation. Alternatively, the glycolate ester oligomers can go from the distillation column to the hydrogenation reactor without additional processing steps. The ethylene glycol employed during esterification can be freshly added to the esterification reaction or obtained as a recycled portion of the crude ethylene glycol product. In another example, purified ethylene glycol may be recycled to the esterification step. Considering the overall material balance, in theory 1 mole of ethylene glycol can be combined with 1 mole of glycolic acid ultimately to produce 2 moles of ethylene glycol, a fraction of which may be recycled to the esterification step, distillation column, and the remainder recovered as product.

The hydrogenation reaction can be conducted in the liquid or the gas phase using known processes. Typically, the glycolate ester oligomers are contacted with hydrogen under pressure in the presence of a catalyst effective for hydrogenation at temperatures from 150 to 300° C. Additional examples of temperatures ranges are from 200 to 250° C. Examples of typical pressure ranges are from 35 bara to 350 bara and 70 bara to 140 bara. Considerable latitude in the temperature and pressure of hydrogenation is possible depending upon the use and choice of hydrogenation catalyst and whether the process is conducted in the liquid or gas phase.

The hydrogenation catalyst may comprise any metal or combination of metals effective for the hydrogenation of esters to alcohols. Typical hydrogenation catalysts include, but are not limited to, at least one metal selected from Groups 8, 9, 10 of the Periodic Table of the Elements (1984 Revision by IUPAC), and copper. In addition, the hydrogenation catalyst may comprise at least one additional metal promoter selected from chromium, magnesium, barium, sodium, nickel, silver, lithium, potassium, cesium, zinc, cobalt, and gold. The term "metal", as used herein in the context of hydrogenation catalysts, is understood to include metals in their elemental form and compounds thereof such as, for example, metal oxides, salts, and complexes with organic ligands. For example, the hydrogenation catalyst can comprise a Raney nickel or a metal oxide. Typical metal oxide catalysts include, for example, copper chromite, copper oxide, or copper oxide in combination with the oxide of magnesium, barium, sodium, nickel, silver, lithium, potassium, cesium, zinc, cobalt, or mixtures thereof. In another example, the hydrogenation catalyst can comprise cobalt metal in combination with zinc and copper oxides.

The hydrogenation step of the process of the present invention may be conducted under continuous, semi-continuous, or batch modes of operation and may utilize a variety of reactor types. Examples of suitable reactor types include, but are not limited to, stirred tank, continuous stirred tank, trickle bed, tower, slurry, and tubular reactors. The catalyst should be dispersed throughout the reaction media to effectively assist contact of reactants and catalyst. The catalyst may be introduced as a liquid or as small particles which are conveniently slurried or suspended in the agitated reaction mixture. Typically, the catalyst is used in the form of a fixed bed or in slurry form through which reactants are continuously circulated in the liquid or gas phase.

FIG. 1 represents one embodiment of the present invention. Glycolic acid and water 3 are fed to distillation column 25 at a feed location above ethylene glycol feed 4. Ethylene glycol feed 4 may comprise ethylene glycol recycled from the hydrogenation of glycolate ester oligomers to ethylene glycol. The configuration of distillation column 25, including the number of stages and the feed locations as well as operating conditions including temperature and pressure, can be selected to produce distillate product 5 and bottoms product 6 of desired compositions. Bottoms product 6 comprises the glycolate ester oligomers. Distillate product 5 comprises water. Distillation column 25 is typically operated to provide bottoms product 6 with a desired mole percent of the total moles of water plus acid-ends and distillate product 5 with a minimum amount of glycolic acid and ethylene glycol.

FIG. 2 represents another embodiment of the present invention. Aqueous formaldehyde 1 and carbon monoxide 2 are fed to hydrocarboxylation reactor 20 to produce hydrocarboxylation effluent 3 comprising glycolic acid and water. The hydrocarboxylation reaction may take place in the presence of a solvent and a homogeneous or heterogeneous acid catalyst. Although not shown in FIG. 2, the solvent, any unreacted formaldehyde, and the catalyst may be separated by means known to those skilled in the art and recycled to hydrocarboxylation reactor 20. Hydrocarboxylation effluent 3, comprising glycolic acid and water, is fed to distillation column 25 at a feed location above ethylene glycol recycle 4. The configuration of the distillation column, including the number of stages and the feed locations as well as operating conditions including temperature and pressure, may be selected to produce distillate product 5 and bottoms product 6 of desired compositions. Bottoms product 6 comprises the glycolate ester oligomers. Distillate product 5 comprises water. Distillation column 25 is typically operated to provide bottoms product 6 with a desired mole percent of the total moles of water plus acid-ends, and distillate product 5 with a minimum amount of glycolic acid and ethylene glycol present.

Bottoms product 6, hydrogen 7, and catalyst feed 13 are fed to hydrogenation reactor 30. Although not shown in FIG. 2, bottoms product 6 may undergo any separation process known to those skilled in the art to further concentrate the glycolate ester oligomers and/or remove water prior to hydrogenation. Hydrogenation reactor 30 is operated under reaction conditions to hydrogenate bottoms product 6 to produce effluent stream 8 comprising ethylene glycol and catalyst. Effluent steam 8 is separated into ethylene glycol 10 and catalyst recycle 9 in catalyst recovery unit 35 by means known to those skilled in the art. Catalyst recycle 9 is combined with catalyst make-up 12 to produce catalyst feed 13 which is added to hydrogenation reactor 30. Ethylene glycol 10 is separated into ethylene glycol recycle 4 and ethylene glycol product 11. Ethylene glycol recycle 4 is fed to distillation column 25.

The invention also includes the following non-limiting embodiments.

Embodiment A is a process for producing glycolate ester oligomers comprising the steps of (a) feeding ethylene glycol, glycolic acid, and water to a reaction zone; (b) reacting the ethylene glycol and the glycolic acid to produce glycolate ester oligomers and glycolic acid oligomers; (c) removing an overhead stream comprising water from the reaction zone; and (d) removing an effluent comprising the glycolate ester oligomers and the glycolic acid oligomers from the reaction zone. The effluent comprises less than 20 mole percent of the total moles of water plus acid-ends.

The process according to Embodiment A, wherein the effluent comprises 5 to 20 mole percent, 7 to 20 mole percent, or 9 to 18 mole percent of the total moles of water plus acid-ends.

The process according to Embodiment A or Embodiment A including any of the intervening features, wherein in step (a) the molar ratio of glycolic acid to ethylene glycol is from 0.1:1 to 10:1, 0.1:1 to 5:1, or 1:1 to 2:1.

The process according to Embodiment A or Embodiment A including any of the intervening features, wherein the overhead stream comprises less than 5 weight percent, less than 1 weight percent, or less than 0.1 weight percent of ethylene glycol and glycolic acid, on a total overhead stream weight basis.

The process according to Embodiment A or Embodiment A including any of the intervening features, wherein no additional catalyst is added to the reaction zone.

The process according to Embodiment A or Embodiment A including any of the intervening features, wherein step (a) further comprises feeding diethylene glycol and/or triethylene glycol.

The process according to Embodiment A or Embodiment A including any of the intervening features, wherein the reaction zone comprises at least one piece of equipment selected from the group consisting of an evaporator, a thin-film evaporator, a wiped-film evaporator, a flash vessel, a rectifying column, a stripping column, and a distillation column.

Embodiment B is a process for producing glycolate ester oligomers comprising the steps of (a) feeding ethylene glycol, glycolic acid, and water to a distillation column; (b) reacting the ethylene glycol and the glycolic acid to produce glycolate ester oligomers and glycolic acid oligomers; (c) removing a distillate product comprising water from the distillation column; and (d) removing a bottoms product comprising the glycolate ester oligomers and the glycolic acid oligomers from the distillation column. The bottoms product comprises less than 20 mole percent of the total moles of water plus acid-ends.

The process according to Embodiment B wherein the bottoms product comprises 5 to 20 mole percent, 5 to 18 mole percent, or 9 to 15 mole percent of the total moles of water plus acid-ends.

The process according to Embodiment B or Embodiment B including any of the intervening features, wherein in step (a) the molar ratio of glycolic acid to ethylene glycol is from 0.1:1 to 10:1, 0.1:1 to 5:1, or 1:1 to 2:1.

The process according to Embodiment B or Embodiment B including any of the intervening features, wherein the distillate product comprises less than 5 weight percent, less than 1 weight percent, or less than 0.1 weight percent of ethylene glycol and glycolic acid, on a total distillate product weight basis.

The process according to Embodiment B or Embodiment B including any of the intervening features, wherein no additional catalyst is added to the distillation column.

The process according to Embodiment B or Embodiment B including any of the intervening features, wherein the base temperature is from 100 to 225° C., 150 to 200° C., or 160 to 185° C.

The process according to Embodiment B or Embodiment B including any of the intervening features, wherein step (a) further comprises feeding diethylene glycol and/or triethylene glycol.

The process according to Embodiment B or Embodiment B including any of the intervening features, wherein the pressure is from 5 to 800 mmHg, 5 to 300 mmHg, or 30 to 200 mmHg.

The process according to Embodiment B or Embodiment B including any of the intervening features, wherein the distillation column comprising 2 to 30 stages, 2 to 15 stages, or 2 to 10 stages.

The process according to Embodiment B or Embodiment B including any of the intervening features, wherein the feeding configuration is selected from one of the group consisting of feeding ethylene glycol, glycolic acid, and water on the same stage, feeding ethylene glycol at a lower stage than glycolic acid and water, feeding ethylene glycol at a higher stage than glycolic acid and water, and feeding ethylene glycol to the reboiler and glycolic acid and water on a stage.

Embodiment C is a process for the production of ethylene glycol comprising the steps of (a) preparing an acid stream comprising glycolic acid by contacting formaldehyde with carbon monoxide and water; (b) feeding the acid stream and a first ethylene glycol stream to a distillation column to produce a distillate product comprising water and a bottoms product comprising glycolate ester oligomers and glycolic acid oligomers; (c) feeding the bottoms product and hydrogen to a hydrogenation reactor to produce a second ethylene glycol stream; (d) separating the second ethylene glycol stream into the first ethylene glycol stream and a product stream; and (e) recycling at least a portion of the first ethylene glycol stream to the distillation column in step (b).

The process according to Embodiment C wherein the bottoms product comprises 5 to 20 mole percent, 5 to 18 mole percent, or 9 to 15 mole percent of the total moles of water plus acid-ends.

The process according to Embodiment C or Embodiment C including any of the intervening features, wherein in step (a) the molar ratio of glycolic acid to ethylene glycol is from 0.1:1 to 10:1, 0.1:1 to 5:1, or 1:1 to 2:1.

The process according to Embodiment C or Embodiment C including any of the intervening features, wherein the distillate product comprises less than 5 weight percent, less than 1 weight percent, or less than 0.1 weight percent of ethylene glycol and glycolic acid, on a total distillate product weight basis.

The process according to Embodiment C or Embodiment C including any of the intervening features, wherein no additional catalyst is added to the distillation column.

The process according to Embodiment C or Embodiment C including any of the intervening features, wherein step (b) further comprises feeding diethylene glycol and/or triethylene glycol.

The process according to Embodiment C or Embodiment C including any of the intervening features, wherein the base temperature is from 100 to 225° C., 150 to 200° C., or 160 to 185° C.

The process according to Embodiment C or Embodiment C including any of the intervening features, wherein the pressure is from 5 to 800 mmHg, 5 to 300 mmHg, or 30 to 200 mmHg.

The process according to Embodiment C or Embodiment C including any of the intervening features, wherein the distillation column comprising 2 to 30 stages, 2 to 15 stages, or 2 to 10 stages.

The process according to Embodiment C or Embodiment C including any of the intervening features, wherein the feeding configuration is selected from one of the group consisting of feeding ethylene glycol, glycolic acid, and water on the same stage, feeding ethylene glycol at a lower stage than glycolic acid and water, and feeding ethylene glycol at a higher stage than glycolic acid and water, and feeding ethylene glycol to the reboiler and glycolic acid and water on a stage.

The invention can be further illustrated by the following examples of preferred embodiments thereof, although it will be understood that these examples are included merely for purposes of illustration and are not intended to limit the scope of the invention.

EXAMPLES

The bottoms product of the reactive distillation process was analyzed as follows. The components of samples were first reacted with BSTFA in the presence of pyridine to the corresponding TMS-derivatives including water, which were then separated and quantified by an internal standard (decane or dodecane) wt % calibrated GC method. The volume ratio of sample to derivatization reagent (BSTFA) and pyridine (containing the internal standard compound) was 0.1 g: 1 ml:0.2 ml in a GC vial, which was heated at 80° C. for 30 minutes to ensure complete derivatization. The GC method uses a DB-1301 capillary column or equivalent (6% cyanopropylphenyl/94% dimethylpolysiloxane stationary phase, 60 meters×0.32 mm ID×1.0 um film thickness), a split injector (at 280° C.), a flame ionization detector (at 300° C.), helium carrier gas at a constant linear velocity of 27 cm/sec (a Shimadzu GC 2010 or equivalent) or at an initial column head pressure of 17 psig, an oven temperature program of 80° C. initial temp for 6 min, 4° C./min temp ramp to 150° C. held for 0 min and 10° C./min temp ramp to 290° C. for 17.5 min final hold time. 1 μl of the prepared sample solution was injected with a split ratio of 40:1. The method provided quantification range of 0.01-100 wt % for each analyte within its separation capability. The method quantified 42 components at wt % levels and 1,2-propanediol and 1,2-butanediol down to 5 ppm by weight in this reaction matrix. Throughout the examples, the following abbreviations are used.

| Name | Structure | Abbreviation |
|---|---|---|
| Glycolic Acid | 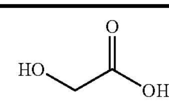 | G1 |
| (2-Hydroxyacetoxy)-acetic acid | 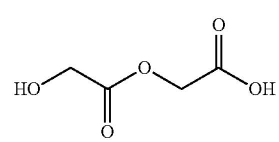 | G2 |
| 2-(2'-Hydroxyacetoxy)-acetoxyacetic acid | 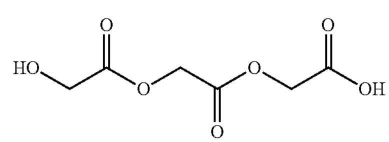 [SMILES: O=C(O)COC(=O)COC(=O)CO] | G3 |
| 2-(2'-(2''-Hydroxyacetoxy)-acetoxy)-acetoxyacetic acid | | G4 |
| Ethylene Glycol | 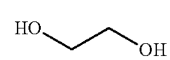 | EG |
| Diethylene Glycol | 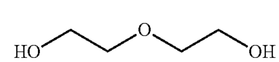 | DEG |

-continued

| Name | Structure | Abbreviation |
| --- | --- | --- |
| 2-Hydroxyethyl 2-hydroxyacetate | 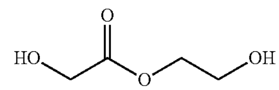 | HGEgH |
| 1,2-Ethanediyl bis(2-hydroxyacetate) | 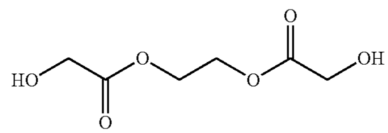 [SMILES: O=C(CO)OCCOC(=O)CO] | HGEgG'H |
| 2''-Hydroxyethyl (2'-hydroxyacetoxy)-acetate | 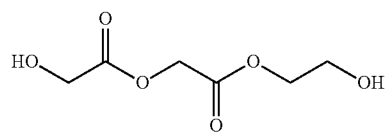 [SMILES: O=C(CO)OCC(=O)OCCO] | HG2EgH |
| 2'-[2''-(2'''-Hydroxyacetoxy)-acetoxy]ethyl 2-hydroxyacetate | 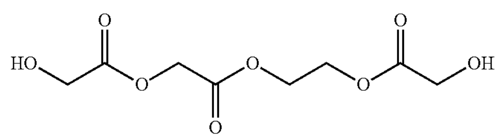 [SMILES: O=C(CO)OCCOC(=O)COC(=O)CO] | HG2EgG'H |
| 2'''-Hydroxyethyl (2'-(2''-hydroxyacetoxy)-acetoxy)acetate | 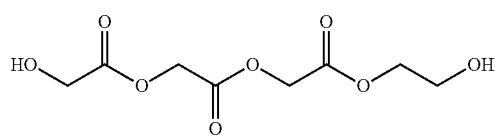 [SMILES: O=C(CO)OCC(=O)OCC(=O)OCCO] | HG3EgH |
| 2'-(2''-[2'''-(2''''-Hydroxyacetoxy)-acetoxy]acetoxy)-ethyl 2-hydroxyacetate | 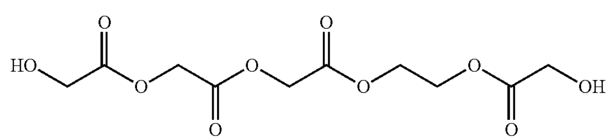 [SMILES: O=C(CO)OCCOC(=O)COC(=O)COC(=O)CO] | HG3EgG'H |
| 2''''-Hydroxyethyl (2'-(2''-(2'''-hydroxyacetoxy)-acetoxy)acetoxy)-acetate | 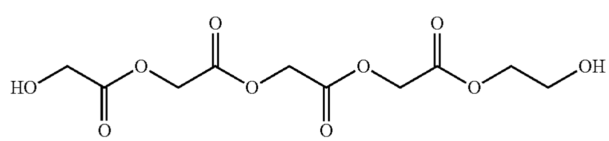 [SMILES: O=C(CO)OCC(=O)OCC(=O)OCC(=O)OCCO] | HG4EgH |
| 2'-[2''-(2'''-Hydroxyacetoxy)-ethoxy]ethyl 2-hydroxyacetate | 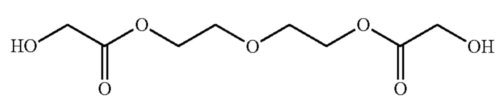 [SMILES: O=C(CO)OCCOCCOC(=O)CO] | HGEg2G'H |
| 2'-(2''-Hydroxyethoxy)-ethyl 2-hydroxyacetate | 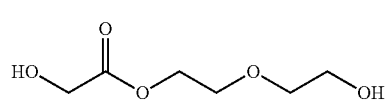 [SMILES: O=C(CO)OCCOCCO] | HGEg2H |

Example 1

Ethylene glycol and aqueous glycolic acid were purchased and used without further processing. A 1 inch Oldershaw column with 30 trays (excluding the condenser and reboiler) was fed aqueous glycolic acid and ethylene glycol at stage 20, counted from the bottom up. The molar feed ratio of glycolic acid to ethylene glycol was targeted at 1:1. The top pressure of the distillation column, as measured at the vacuum pump, was maintained at 250 mmHg. The column reboiler was glass jacketed and heated with oil from an external oil bath such that the base temperature was controlled at 165° C. The reactive distillation column was run long enough to ensure steady state performance. Two composition measurements were taken 60 minutes apart in time. The reactive distillation column conditions and results are shown in Tables 1 and 2. The Bottoms composition of water plus acid-ends for each sample measurement is listed in Table 2 as sample 1(a) and 1(b), respectively.

TABLE 1

Average Reactive Distillation Material Balances - measured feed and take-off streams for course of run

| Example | Average Glycolic Acid Feed stream (g/min) (a) | Average Moles G1 mole/min | Average Ethylene Glycol Feed (g/min) (b) | Average moles EG (moles/min) | Average Bottoms Product (g/min) | Total Distillate Product (g/min) (c) |
|---|---|---|---|---|---|---|
| 1 | 1.32 | 0.011 | 0.76 | 0.012 | 1.52 | 0.54 |
| 2 | 1.28 | 0.011 | 0.75 | 0.012 | 1.46 | 0.52 |
| 3 | 1.32 | 0.011 | 0.38 | 0.006 | 1.07 | 0.55 |
| 4 | 1.32 | 0.011 | 0.50 | 0.008 | 1.18 | 0.53 |
| 5 | 1.33 | 0.011 | 0.44 | 0.007 | 1.12 | 0.58 |
| 6 | 1.34 | 0.011 | 0.44 | 0.007 | 1.12 | 0.49 |
| 7 | 1.33 | 0.011 | 0.44 | 0.007 | 1.11 | 0.46 |
| 8 | 1.35 | 0.011 | 0.50 | 0.008 | 1.17 | 0.55 |
| 9 | 1.37 | 0.011 | 0.48 | 0.008 | 1.17 | 0.45 |

(a) Analytical results showed the glycolic acid feed to contained 63.0 wt % Glycolic Acid, 34.1 wt % water, 1.3 wt % diglycolic acid, and 1.6 wt % other.
(b) Ethylene Glycol feed was assumed to be 100 wt % Ethylene Glycol.
(c) Each distillate product contained less than 0.5 wt % of glycolic acid and ethylene glycol.

TABLE 2

Laboratory reactive distillation examples

| Example | Feed stage Acid | Feed stage EG | Pressure (mmHg) | Temp (° C.) | Feed Acid:EG molar ratio | Bottoms Mole % water plus acid-ends (a) | Bottoms Mole % water plus acid-ends (b) |
|---|---|---|---|---|---|---|---|
| 1(a)/(b) | 20 | 20 | 250 | 165 | 0.9:1 | 19.0 | 15.9 |
| 2(a)/(b) | 20 | 20 | 250 | 175 | 0.9:1 | 14.4 | 14.8 |
| 3(a)/(b) | 20 | 20 | 250 | 175 | 1.8:1 | 18.7 | 18.6 |
| 4(a)/(b) | 12 | 12 | 150 | 176 | 1.4:1 | 16.6 | 16.4 |
| 5(a)/(b) | 20 | 12 | 150 | 165 | 1.6:1 | 22.6 | 21.8 |
| 6(a) | 20 | 12 | 150 | 155 | 1.6:1 | 27.5 | — |
| 7(a)/(b) | 20 | 12 | 75 | 155 | 1.6:1 | 24.5 | 26.3 |
| 8(a)/(b) | 20 | 12 | 50 | 175 | 1.4:1 | 18.7 | 18.8 |
| 9(a)/(b) | 20 | 12 | 30 | 175 | 1.4:1 | 13.8 | 15.2 |

One skilled in the art can calculate a basic column material balance given the data listed in Table 1. Example 1 had a 1.52 g/min of glycolic acid feed which was 63 wt % glycolic acid which calculated to an average glycolic acid molar feed rate of 0.011 moles/min (i.e., 1.32*0.63/76). The total molar feed rate of EG was 0.012 moles/min (i.e., 0.76/62).

A detailed example calculation of the mole percent water plus acid-ends is given for Example 1(a). Table 3 lists the analytical results for the glycolic acid, ethylene glycol, glycolic acid oligomers, and glycolate ester oligomers in the bottoms product for Example 1(a). Table 3 also lists the number of glycolic acid moiety and ethylene glycol moiety for each molecule and the calculated moles of glycolic acid moiety and ethylene glycol moiety for a 100 gram basis of bottoms product. The water concentration in the bottoms product is 1.78 wt % or 0.0989 moles on a 100 gram weight basis. The total moles of water plus acid-ends is 0.0989+0.1778+0.0195+0.0018+0.0003 which equals 0.2982. The total moles of glycolic acid moiety plus ethylene glycol moiety equals 1.4619. Therefore the mole percent of the total moles of water plus acid-ends is the sum of the moles of water plus moles of acid-ends divided by the sum of the moles of water plus the moles of glycolic acid moiety plus the moles of ethylene glycol moiety, or 0.2982/(0.0989+1.4619) times 100% which equals 19.0% as shown for Example 1(a) in Table 2.

TABLE 3

Detailed analysis of Bottoms mole percent water plus acid-ends

| Compound in Bottoms product | Wt % by GC | Molecular weight | # of G1 moieties/molecule | # of EG moieties/molecule | Moles acid-ends | Moles G1 and EG moieties |
|---|---|---|---|---|---|---|
| G1 | 13.51 | 76 | 1 | 0 | 0.1778 | 0.1778 |
| G2 | 2.61 | 134 | 2 | 0 | 0.0195 | 0.0389 |
| G3 | 0.35 | 192 | 3 | 0 | 0.0018 | 0.0055 |
| G4 | 0.07 | 250 | 4 | 0 | 0.0003 | 0.0011 |
| EG | 22.04 | 62 | 0 | 1 | 0 | 0.3549 |
| HGEgH | 38.59 | 120 | 1 | 1 | 0 | 0.6426 |
| HGEgG'H | 7.25 | 178 | 2 | 1 | 0 | 0.1221 |
| HG2EgH | 4.65 | 178 | 2 | 1 | 0 | 0.0783 |
| HG2EgG'H | 1.81 | 236 | 3 | 1 | 0 | 0.0307 |
| HG3EgG'H | 0.31 | 294 | 4 | 1 | 0 | 0.0053 |
| HGEg2G'H | 0.22 | 222 | 2 | 2 | 0 | 0.0040 |
| HGEg2H | 0.04 | 164 | 1 | 2 | 0 | 0.0007 |

Examples 2-7

Examples 2 through 7 were run in the same manner as Example 1 except the feed location, top pressure, bottom temperature, and/or molar feed ratio were varied as given in Table 1. For all Examples except for Example 6, multiple measurements were made during the experiment. These measurements were taken between 30 and 90 minutes apart in time and are listed as (a) and (b) results for each Example.

Examples 8 and 9

Examples 8 and 9 were run in the same manner as Example 1 except, in addition to changes in the feed location, top pressure, bottom temperature, and/or molar feed ratio as given in Table 1, trace components were added to the glycolic acid feed such that the glycolic acid feed stream contained 1 wt % formic acid, 1.3 wt % oxydiacetic acid, 0.59 wt % methoxyacetic acid, and 0.0132 wt % formaldehyde. The formic acid, methoxyacetic acid, and glycolic acid distributed essentially completely to the bottoms product. The formaldehyde material balance was not internally consistent. In addition to formaldehyde being present in a small quantities and consequently relative susceptible to measurement error, glycolic acid can decompose to form formaldehyde. Additionally, the experimental set-up had a much higher residence time in the base of the distillation column than would be present in a commercial set-up, causing a greater amount of formaldehyde formation. The formaldehyde appeared to split approximately 25 mole % to the bottoms product and approximately 75 mole % to the distillate product.

We claim:

1. A process for producing glycolate ester oligomers comprising:
    (a) feeding ethylene glycol and aqueous glycolic acid to a reaction zone, wherein said aqueous glycolic acid comprises 50 to 95 weight percent glycolic acid, based on the total weight of said aqueous glycolic acid;
    (b) reacting said ethylene glycol and said glycolic acid to produce glycolate ester oligomers and glycolic acid oligomers;
    (c) removing an overhead stream comprising water from said reaction zone; and
    (d) removing an effluent comprising said glycolate ester oligomers and said glycolic acid oligomers from said reaction zone, wherein said effluent comprises less than 20 mole percent of the total moles of water plus acid-ends.

2. The process according to claim 1, wherein said effluent comprises from 5 to 18 mole percent of said total moles of water plus acid-ends.

3. The process according to claim 1, wherein in step (a) the molar ratio of said glycolic acid to said ethylene glycol is from 0.1:1 to 10:1.

4. The process according to claim 1, wherein said overhead stream comprises less than 5 weight percent of said ethylene glycol and said glycolic acid, on a total overhead stream weight basis.

5. The process according to claim 1, wherein step (a) further comprises feeding at least one of the group consisting of diethylene glycol and triethylene glycol.

6. The process according to claim 1, wherein said reaction zone comprises at least one piece of equipment selected from the group consisting of an evaporator, a thin-film evaporator, a wiped-film evaporator, a flash vessel, a rectifying column, a stripping column, and a distillation column.

7. A process for producing glycolate ester oligomers comprising:
(a) feeding ethylene glycol and aqueous glycolic acid to a distillation column, wherein said aqueous glycolic acid comprises 50 to 95 weight percent glycolic acid, based on the total weight of said aqueous glycolic acid;
(b) reacting said ethylene glycol and said glycolic acid to produce glycolate ester oligomers and glycolic acid oligomers;
(c) removing a distillate product comprising water;
(d) removing a bottoms product comprising said glycolate ester oligomers and said glycolic acid oligomers,
wherein said bottoms product comprises less than 20 mole percent of the total moles of water plus acid-ends.

8. The process according to claim 7, wherein said bottoms product comprises from 5 to 18 mole percent of said total moles of water plus acid-ends.

9. The process according to claim 8, wherein said bottoms product comprises from 9 to 15 mole percent of said total moles of water plus acid-ends.

10. The process according to claim 7, wherein in step (a) the molar ratio of said glycolic acid to said ethylene glycol is from 0.1:1 to 10:1.

11. The process according to claim 10, wherein said molar ratio of said glycolic acid to said ethylene glycol is from 1:1 to 2:1.

12. The process according to claim 7, wherein said distillate product comprises less than 1 weight percent of the total amount of said ethylene glycol and said glycolic acid, on a total distillate product weight basis.

13. The process according to claim 12, wherein said distillate product comprises less than 0.1 weight percent of the total amount of said ethylene glycol and said glycolic acid, on a total distillate product weight basis.

14. The process according to claim 7, wherein step (a) further comprises feeding at least one of the group consisting of diethylene glycol and triethylene glycol.

15. The process according to claim 7, wherein said distillation column has a base temperature from 100 to 225° C. and a column pressure from 5 to 800 mmHg.

16. The process according to claim 15, wherein said base temperature is from 160 to 185° C. and said column pressure is from 5 to 300 mmHg.

17. The process according to claim 7, wherein said distillation column comprises from 2 to 30 stages and the feeding configuration is selected from one of the group consisting of feeding said ethylene glycol, said glycolic acid, and said water on the same stage, feeding said ethylene glycol on a lower stage than said glycolic acid and said water, feeding said ethylene glycol on a higher stage than said glycolic acid and said water, and feeding said ethylene glycol to the reboiler and said glycolic acid and said water on a stage.

* * * * *